US006413999B1

(12) United States Patent
Juurlink et al.

(10) Patent No.: US 6,413,999 B1
(45) Date of Patent: Jul. 2, 2002

(54) TREATMENT FOR ACUTE PHYSICAL INSULT TO THE CENTRAL NERVOUS SYSTEM

(75) Inventors: Bernhard Juurlink; Robert Griebel; Huse Kamencic; Phyllis Paterson, all of Saskatoon (CA)

(73) Assignee: University of Saskatchewan Technologies Inc., Saskatoon (CA)

( * ) Notice: Subject to any disclaimer, the term of this patent is extended or adjusted under 35 U.S.C. 154(b) by 0 days.

(21) Appl. No.: 09/640,020

(22) Filed: Aug. 17, 2000

Related U.S. Application Data

(60) Provisional application No. 60/149,249, filed on Aug. 17, 1999.

(51) Int. Cl.$^7$ ............................................. A61K 31/425
(52) U.S. Cl. ....................................................... 514/369
(58) Field of Search ......................................... 514/369

(56) References Cited

U.S. PATENT DOCUMENTS

| | | | |
|---|---|---|---|
| 4,335,210 | A | 6/1982 | Meister et al. |
| 4,426,378 | A | 1/1984 | Holaday |
| 4,775,675 | A | 10/1988 | Gyorgydeak et al. |
| 5,095,027 | A | 3/1992 | Goldberg et al. |
| 5,095,029 | A | 3/1992 | Kleefeld et al. |
| 5,208,249 | A | 5/1993 | Rowe et al. |
| 5,750,507 | A | 5/1998 | Ozawa et al. |
| 5,780,489 | A | 7/1998 | Brooks |
| 5,824,693 | A | 10/1998 | Goldberg |
| 5,846,988 | A | 12/1998 | Hellberg |
| 5,863,906 | A | 1/1999 | Arnal et al. |

FOREIGN PATENT DOCUMENTS

| | | |
|---|---|---|
| CA | 2110488 | 1/1993 |
| CA | 2096036 | 2/1994 |
| CA | 2113759 | 8/1994 |
| CA | 2136578 | 5/1996 |
| CA | 2219894 | 12/1996 |
| CA | 2225526 | 1/1997 |
| CA | 2231438 | 3/1997 |
| CA | 2242396 | 8/1997 |
| CA | 2219606 | 4/1998 |
| EP | 0 501 637 A2 | 2/1992 |
| EP | 0 583 863 A1 | 4/1993 |
| WO | WO 98/29101 | 7/1998 |

OTHER PUBLICATIONS

Bangalore et al. "Selective Modulation of Glutathione in Mouse Brain Regions and its Effect on Acrylamide–Induced Neurotoxicity", Biochemical Pharmacology, vol. 43, No. 2, pp. 263–269, 1992.

Hazelton et al. "Effects of Cysteine Pro–Drugs on Acetaminophen–Induced Hepatotoxicity", The Journal of Pharmacology and Experimental Therapeutics, vol. 237, No. 1, pp. 341–349, 1986.

Anderson et al. "Marked Increase of Cystein Levels in Many Regions of the Brain after Administration of 2–Oxothiazolidine–4–Carboxylate", FASEB Journal, vol. 3, No. 5, pp. 1632–1636, 1989.

Mesina et al. "Administration of L–2–Oxothiazolidine–4–Carboxylate Increases Glutathione Levels in Rat Brain", Brain Research, vol. 478, pp. 181–183, 1989.

Pileblald et al. "Increase in Rat Brain Glutathione Following Intracerebroventricular Administration of y–Glutamylcystein", Biochemical Pharmacology, vol. 44, No. 44, No. 5, pp. 895–903, 1992.

Meister et al. "Intracellular Cysteine and Clutathione Delivery Systems", Journal of the American College of Nutrition, vol. 5, No. 2, pp. 137–151, 1986.

Juurlink B. et al. *The Journal of Spinal Cord Medicine*, vol. 21, vol. 21, No. 4, (1998), "Review of oxidative stress in brain and spinal cord injury" p. 309.

Gerard–Monnier, D., et al., (1993) "Partial prevention of glutathione depletion in rats following acute intoxication with diethylmaleate", Clinical Physiology and Biochemisty, 1993, 10:36–42.

Cudkowicz, M.E., Sexton, P.M., Ellis, T., Hayden, D.L., Gwilt, P.R., Whalen, J., and Brown, R.H., Jr. (1999) The pharmacokinetics and pharmaco–dynamics of Procysteine in amyotrophic lateral sclerosis. Neurology 52, 1492–1491.

Dringen, R., and Hamprecht, B. (1999) N–acetylcysteine, but not methione or 2–oxothiazolidine–4–carboxylate, serves as cysteine donor for the synthesis of glutathione in cultured neurons derived from embryonal rat brain. Neurosci Lett 259, 79–82.

Vita, Joseph, (1998), "L–2–oxothiazolidine–4–carboxylic acid reverses and dicileo endothelial dysfunction in patients with coronary artery disease", *J. Clin. Invest.*. 101 (6):1408–1414.

Levy, Mark, "Selective elevation of gluthatione levels in target tissues with L–2–oxothiazolidine–4 carboxylate (OTC) protects against hyperoxia–induced lung damage in protein–energy malnourished rats: Implications for a new treatment strategy", *J. Nutr.* 128:671–676, (1998).

Paterson, Phyllis G.; Juurlink, Bernhard H.J. SO—Neurotoxic. Res. (1999), 1(2), 99–112 (abstract only).

Lucas, J., et al., Journal of Neuropathology and Experimental Neurology; vol. 57, No. 10 Oct., 1998 pp. 937–954.

*Primary Examiner*—William R. A. Jarvis
(74) *Attorney, Agent, or Firm*—Ridout & Maybee LLP

(57) ABSTRACT

A method of promoting functional recovery and reducing oxidative stress and inflammation following an acute physical insult to the central nervous system, comprising administering to a mammalian patient which has suffered an acute physical insult to the central nervous system an initial dose of L-2-oxothiazolidine-4-carboxylate ("OTC") or a variant thereof is disclosed. This method preferably further includes the step of administering a number of subsequent doses of OTC or a variant thereof as subsequent time periods. Also provided is a use of OTC or a variant thereof in the preparation of a medicament useful in reducing inflammation in the central nervous system and promoting the functional recovery of a mammalian patient which has suffered an acute physical insult to the central nervous system, such as neurotrauma, stroke or aneurysm.

29 Claims, 10 Drawing Sheets

Stroke-Induced Brain Damage In Animals Treated With OTC Or Saline Vehicle

TREATMENT FOR ACUTE PHYSICAL INSULT TO THE CENTRAL NERVOUS SYSTEM

This application claims priority to provisional application No. 60/149,249, filed Aug. 17, 1999.

FIELD OF THE INVENTION

The invention relates to the treatment of patients suffering from neurotrauma, and particularly to methods for improving recovery from neurotrauma using procysteine compounds such as N-acetyl cysteine ("NAC") and L-2-oxothiazolidine-4-carboxylate ("OTC") or its variants.

BACKGROUND OF THE INVENTION

Acute physical insult to the central nervous system ("CNS") very often leads to paraplegia, quadriplegia, speech and motor defects and other physical and mental conditions which impose a large burden on the individual afflicted, family and friends as well as society at large. Damage due to the primary mechanism of injury is generally aggravated by secondary mechanisms of injury including oxidative stress and accompanying inflammation. Secondary mechanisms of injury frequently cause greater tissue damage than the initial insult and can cause damage not only at the site of original injury but at adjacent sites as well.

Acute physical insult to the CNS ("insult") includes a wide range of sudden physical perturbations, including neurotrauma and vascular events such as stroke and aneurysm. Insult is distinguished from other disruption of the CNS such as ALS and neurotoxic compound poisoning by the nature of the injury and physiological responses resulting from the rapid onset and physical interference with CNS function associated with insult.

One approach to treating patients following insult is to repair the damage, for example, by promoting axon regeneration or through introduction of embryonic stem cells that differentiate and possible re-establish some of the disrupted circuitry; these are technically challenging approaches and so far have only been attempted in experimental animals.

A second approach is to minimize secondary mechanisms of tissue damage following insult. Prevention of damage is a much more efficacious treatment of neurotrauma than to attempt to repair damage once it has occurred. To date no fully satisfactory means of diminishing secondary damage following neurotrauma is available.

Unfortunately, efforts to reduce secondary damage have been hampered by difficulties in delivering suitable medicaments to the CNS. The blood-brain barrier normally restricts the passage of many molecules, and may prevent or delay delivery beyond the time available for full efficacy. Insult causes further changes in permeability and transport, further complicating treatment efforts.

Previous work has focused on reducing secondary injury following insult through the administration of methylprednisolone. However, studies to date suggest that methylprednisolone provides for only modest functional improvement and may lead to significant adverse side-effects.

L-2-oxothiazolidine-4-carboxylate ("OTC") and N-acetylcysteine ("NAC") prodrugs which are believed to be useful in increasing glutathione (GSH) levels in tissues. GSH is believed to play a role in protecting tissues from damage due to oxidative stress.

It has been shown that pre-treatment of cultured neurons in vitro with OTC permits increased survival when the pre-treated neurons are subsequently injured. Moreover, in some studies where subjects were treated with OTC prior to the administration of neurotoxic GSH-depleting compounds, pre-treatment with OTC was reported to reduce the severity of GSH depletion observed. However, these examples are limited to situations where OTC was administered under normal, non-injured conditions where the normal permeability of the blood-brain barrier and the neuronal cell membrane does not appear to have been significantly altered.

It has been suggested that OTC may act by direct interaction of cysteine (formed from OTC) with the GSH-depleting compound, thereby reducing the demand for endogenous GSH. Thus, this mechanism of GSH preservation may be specific to GSH-depleting compounds and may not function in cases of GSH depletion arising from acute physical insult to the CNS (Gerard-Monnier, et al., *Clin. Physiol. Biochem.*, 10:36–42, 1993).

Studies to date have focused on the use of OTC administered either prior to or substantially simultaneous with the administration of neurotoxic compounds. However, actual incidents of insult, for example in vehicle accidents, work place injuries, stroke or aneurysm usually occur several minutes or hours prior to the administration of expert medical attention and medication. This is particularly problematic as prior reports have tended to show either no increase in GSH concentrations immediately following OTC administration (a critical period for the control of secondary injury), or a decrease in GSH-concentrations during this period. Thus, the prior art suggests that OTC is poorly suited to use to improve functional recovery following insult.

Acute physical insult to the CNS causes disruptions in normal blood flow which may affect drug delivery and vascular permeability. In particular, blood flow may be disrupted at the site of injury and adjacent sites. This may interfere with the delivery of blood-born medicaments such as OTC.

Oxidative stress, including that resulting from insult, causes numerous cellular changes in affected neurons and glial cells as well as the endothelium of the blood vessels supplying the site of insult and adjacent sites. Among these are alterations in normal cell surface receptors and transport mechanisms. Thus, cells of the CNS experiencing oxidative stress do not necessarily take up some compounds which they would take up under normal conditions. In light of the changes to vascular and cellular permeability upon insult and resultant oxidative stress, it is unclear, in light of the prior art, if OTC could pass through the blood-brain barrier and be taken up by neurons in sufficient amounts following insult. Furthermore, it is not clear that the uptake of OTC, if it occurred, would result in descreased inflammation or improved functional recovery.

Thus, it is an object of the present invention to provide a method of improving functional recovery from insult.

SUMMARY OF THE INVENTION

In one embodiment of the invention there is provided a method of promoting functional recovery from an acute physical insult to the central nervous system, comprising administering to a mammalian patient which has suffered an acute physical insult to the central nervous system an initial dose of OTC, NAC or variants thereof.

In another embodiment of the present invention there is provided a method of promoting functional recovery from an acute physical insult to the central nervous system, comprising administering to a mammalian patient which has suffered an acute physical insult to the central nervous system an initial dose of OTC, NAC or a variants thereof following the insult and administering a number of subsequent doses of OTC or a variant thereof at subsequent time periods.

In another embodiment of the present invention there is provided a method of reducing oxidative stress in the central nervous system of a mammalian patient which has suffered an acute physical insult to the central nervous system, comprising administering an initial dose of OTC or a variant thereof to the patient following the insult.

In another embodiment of the present invention there is provided a method of reducing inflammation in the central nervous system of a mammalian patient which has suffered an acute physical insult to the central nervous system, comprising administering an initial dose of OTC or a variant thereof to the patient following the insult.

In another embodiment of the present invention there is provided a use of OTC or a variant thereof in the preparation of a medicament useful in promoting functional recovery of a mammalian patient which has suffered an acute physical insult to the central nervous system.

In another embodiment of the present invention there is provided a use of OTC or a variant thereof in the preparation of a medicament useful in reducing inflammation in the central nervous system of a mammalian patient which has suffered an acute physical insult to the central nervous system. Use of a combination of methylprednisolone and OTC or a variant thereof in the preparation of a medicament useful in promoting functional recovery of a mammalian patient which has suffered an acute physical insult to the central nervous system.

In another embodiment of the present invention there is provided a use of a combination of methylprednisolone and OTC or a variant thereof in the preparation of a medicament useful in reducing inflammation in the central nervous system of a mammalian patient which has suffered an acute physical insult to the central nervous system.

In another embodiment of the present invention there is provided a use of a combination of methylprednisolone and OTC or a variant thereof in the preparation of a medicament useful in reducing oxidative stress in the central nervous system of a mammalian patient which has suffered an acute physical insult of the central nervous system.

DETAILED DESCRIPTION OF THE PREFERRED EMBODIMENTS

Figure 1:
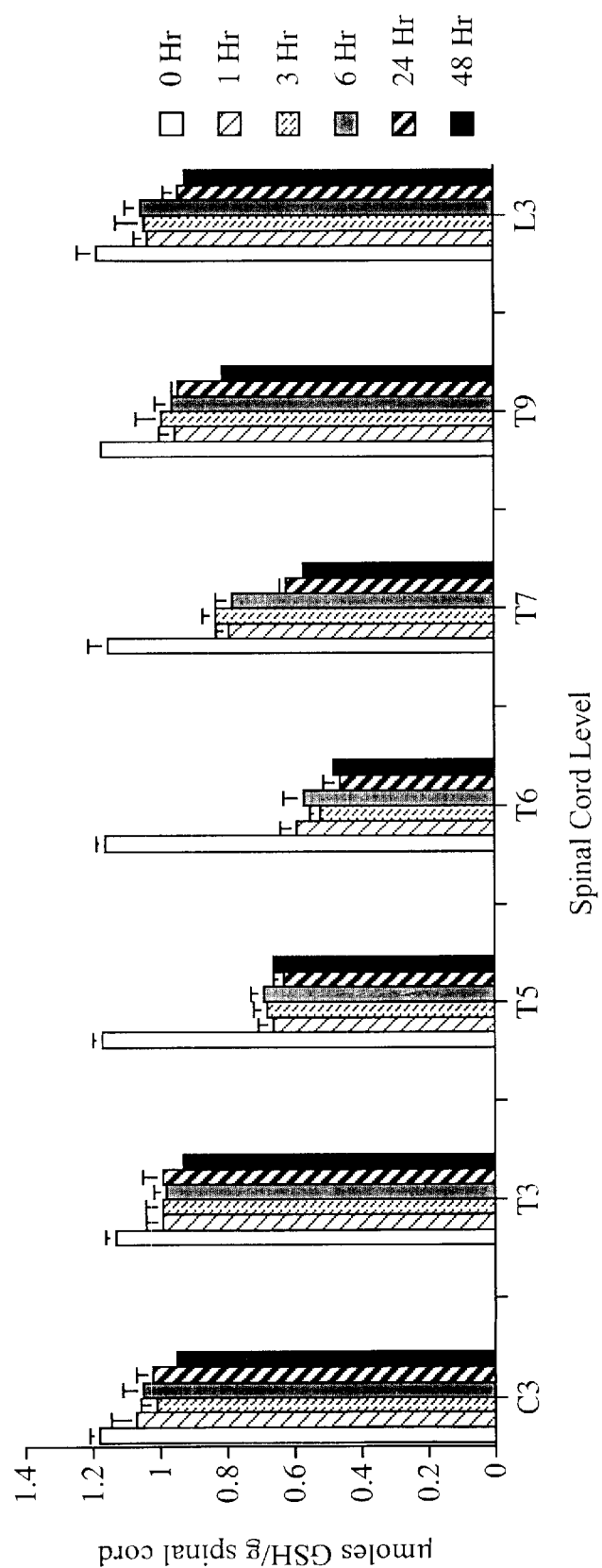
FIG. 1 is a graphical representation of the results of Example 2.

Surprisingly, a method of administering OTC, NAC or variants thereof to effectively reduce oxidative stress and tissue damage and improve functional recovery following insult has been developed.

Preferably, an initial dose of OTC, NAC, or a variant is administered within a first time period following insult. Even more preferably, following the administration of the initial dose, a number of subsequent doses are administered at subsequent time periods. The term "subsequent time period" refers to the period of time between the administration of consecutive doses of NAC or OTC and includes the period of time between the administration of the initial dose and a first subsequent dose, as well as periods of time between the administration of consecutive subsequent doses. It will be appreciated that more than one "subsequent dose" and more than one "subsequent time period" may be employed in a single treatment regimen.

The route of administration is preferably intravenous injection. However, other routes, such as intraperitoneal, subcutaneous or intramuscular injection, or ingestion of appropriately encapsulated or coated compounds will also work.

The first time period may be any appropriate time period. Preferably the first time period is up to 24 hours following insult. More preferably, the first time period is up to 12 hours. Even more preferably, the first time period is up to 6 hours. Yet more preferably, the first time period is up to 2 hours following insult. While it is generally preferable to administer the initial dose as soon as possible following insult, it will be readily understood that the first time period may be selected from a variety of times, in light of the practical limitations of each case.

The subsequent time periods may be any suitable time periods. The exact subsequent time periods can be readily determined by one skilled in the art in light of the disclosure contained herein, the age, gender, size and condition of the patient and the initial and subsequent dose and pharmacokinetic properties of NAC, OTC or the variant administered. Preferably, each subsequent time period will be independently selected to be between about 4 and 16 hours. More preferably, each subsequent time period will be independently selected to be between 8 and 12 hours.

The initial dose may be readily determined by one skilled in the art in light of the disclosure contained herein, based on the size, age, gender and condition of the patient, the severity of the insult, the first time period, other medications received by the patient, and the identity of the variant, NAC or OTC administered and the route of administration. In some cases, an initial dose of between about 0.5 to 20 mmole/kg body weight will be desirable. Preferably, the initial dose is between about 1 and 12 mmole/kg body weight.

The subsequent dose can be readily determined by one skilled in the art in light of the disclosure contained herein, the initial dose, the subsequent time period, the age, gender, size and condition of the patient, other medications received by the patient, and the pharmacokinetic properties of NAC, OTC or the variant administered and the route of administration. In some cases, each subsequent dose will be independently selected to be between about 0.5 and 5 mmole/kg body weight. The subsequent dose may vary from administration to administration, for example to account for the recovery of the patient, or changes in other medications or regimens of treatment over time.

The number of subsequent doses may be any suitable number and can be readily determined by one skilled in the art in light of the disclosure contained herein, the severity of the insult, the condition of the patient, the initial dose, the subsequent dose, the initial time period, the subsequent time period and the pharmacokinetics of the variant, NAC or OTC administered. Generally, subsequent doses will be every 8 or 12 hours and will extend over 2–3 days and sometimes for up to 5 days or longer.

It is generally preferable to maintain OTC levels is plasma of about 50 μm to 150 μm, more preferably about 80 μm to 120 μm. However, depending on the route and frequency of administration, it may be necessary in some cases to increase OTC levels in plasma to significantly higher levels and permit decreases to lower levels before a subsequent administration. It may also be desirable to increase OTC levels in plasma above 150 μM shortly after insult to further reduce secondary injury. Thus, in some cases it will be desirable to increase OTC levels in plasma to between about 1 mM and 3 mM, more preferably between about 1.5 mM and 2.5 mM, and even more preferably between 1.8 mM and 2.2 M; and permit these levels to decline to below 100 μM before administering a subsequent dose of OTC.

It is within the capacity of one skilled in the art to determine an appropriate initial dosage, subsequent dosages, subsequent time periods and the number of subsequent doses for different patients, including human patients, in light of the disclosure contained herein, the severity of the insult and the age, gender, size and condition of the patient. The pharmacokinetic properties of OTC are known in the art, as are methods to readily assess the pharmokinetic properties of variants of OTC. For example, see: P. Porta et al. (1991), *J. Pharmacol. Exp. Therapeutics*, 257:331–334, and R. C. Kalayjian et al. (1994) *J. Acquired Immune Deficiency Syndromes*.

In some situations it will be desirable to administer a variant of OTC. Variants of OTC include, without limitation, esters and pharmaceutically acceptable salts of OTC having the biological activity of OTC, although this activity may be greater or lesser than OTC on a per mole or per gram basis. A substance will have the biological activity of OTC where it is capable of: (a) passing through the blood-brain barrier and entering neurons in a mammalian patient within 4 hours of that patient suffering insult; and, (b) effecting, directly or indirectly, an increase in GSH levels in uninjured mammalian brain within 4 hours of administration by intravenous injection at a dose of 12 mmoles/kg body weight. For example, variants of OTC are described in U.S. Pat. No. 5,208,249 of Rowe et al. and U.S. Pat. No. 5,780,489 of Brooks et al. In light of the disclosure contained herein, it is within the capacity of one skilled in the art to identify variants of OTC within undue experimentation.

In some situations, it will be desirable to administer OTC or a variant thereof together with a second substance which may be a different variant or OTC, or may be a distinct anti-inflammatory compound or an anti-oxidant compound such as methylprednisolone. A combination of a suitable anti-inflammatory compound or anti-oxidant compound and OTC or a variant thereof is useful in reducing oxidative stress and inflammation and promoting functional recovery of a mammalian patient which has suffered an acute physical insult to the central nervous system.

Oxidative stress may be assessed by reference to decreases in tissue GSH, decreases in tissue glutathione reductase activity and increases in protein carbonyl content. Within 1 hour following insult in control animals significant decreases in GSH in the area of injury may be observed, with the greatest decrease generally seen at the site of injury and immediately adjacent thereto. GSH levels are significantly decreased not only in the area of insult but throughout the affected CNS region, likely reflecting oxidative stress accompanying the prominent inflammatory changes observed. Severe oxidative stress at the site of injury and immediately adjacent segments was indicted by a significant decrease in activity of glutathione reductase in the area of insult and an increase in protein carbonyl content 24 hours following neurotrauma.

A marked increase in intercellular adhesion molecule-1 (ICAM-1) and inducible nitric oxide synthase (iNOS) occurs 24 hours following insult, indicating significant levels of inflammation in the CNS. These marked inflammatory changes were correlated with the presence of infiltrating inflammatory leukocytes.

Thus, one would except to observe oxidative stress and inflammation-related alterations in the blood-brain barrier, complicating the delivery of blood-born medicaments such as OTC.

Surprisingly, the administration of an initial dose of OTC following insult results in an increased GSH concentration in the CNS. Thus, the method of the present invention provides a means for delivering OTC to the CNS following insult. GSH concentration increases are associated with an overall decrease in oxidative stress experienced by the CNS of OTC-treated subjects. Thus, administration of OTC significantly reduced oxidative stress following insult. Surprisingly, the administration of an initial dose of OTC following insult also reduces inflammation.

The method of OTC administration and the use of OTC disclosed herein enhance sparing of white matter at the injured region. Thus, functional recovery is enhanced in these subjects.

The 50 gram aneurysm clip model of neurotrauma (applying a crush injury at spinal cord segment T6) was chosen since it has been demonstrated to give consistent results. These results can be generalized to other causes of insult in humans and other mammals. In particular, the 50 g aneurism clip model provides a means to assess the efficacy of treatment for insult such as that typically observed in motor vehicle accidents, sports-related injuries, shooting injuries and work-related accidents.

A modified Levine model of insult by vascular event was chosen. This model is a useful predictor of the efficacy of treatments following insult by vascular events, including stroke and aneurysm.

EXAMPLE 1A

Surgical Procedures For Neurotrauma

Adult male Wistar rats (~320 g) were obtained from Charles River Canada and housed in a temperature-regulated animal facility, exposed to a 12 hour light/dark cycle and had free access to food and water. Animals were treated in accordance with the guidelines of the Canadian Council on Animal Care. Prior in surgery, the rats received the analgesic Buprenorphine-hydrochloride subcutaneously at a dose of 0.05 mg/kg and then every 12 hours for the first 72 hours following surgery. Anesthesia was performed with Halothane (5% induction and 1% maintenance). Laminectomy was performed aseptically at T5-T6 to expose the spinal cord. A 5-second clip compression injury was induced at the T6 spinal cord level using a modified Kerr-Lougheed aneurysm clip with a calibrated force of 50 g as described in Rivlin et al. (*Surg. Neurol.*, 9, 39–43, 1979) and Khan et al. (*Can. J. Neurol. Sci.*, 10, 161–165, 1983). For delivery of drug or saline vehicle a sterile catheter was placed subcutaneously running from the dorsum to enter the peritoneal cavity ventrally; this was done before the laminectomy was performed. Thirty minutes following spinal cord compression an initial dose of OTC or phosphate-buffered saline vehicle ("saline") was delivered intraperitoneally and then subsequent doses were administered every 12 hours for the next five days. The initial dose of OTC was 12 mmoles/kg body weight with subsequent doses of 4 mmoles/kg body weight. Animals were closely observed for behavior, eating and drinking as well as weight loss for the first 12 hours and thereafter at a minimum of three times daily.

Prior to surgery animals weighed 328.3±4.2 g. The weight of saline-treated animals 6 weeks after surgery increased to 403.9±9.5 g while the weight gain of OTC-treated animals was significantly greater (P=0.0337, two-tailed Student's t-test) at 434.3±9.3 g.

Data for all experiments are expressed as means±SEM. Where SEMs are not visible, they are smaller than the symbols. Statistical analyses were performed with the program InStat™.

EXAMPLE 1B

Surgical Procedures For Vascular Events

Nine to eleven week old rats were obtained and housed as described in Example 1A. Animals were treated in accordance with the guidelines of the Canadian Council on Animal Care.

The rats were randomly divided into two groups. Both groups of rats underwent unilateral carotid artery ligation and were then subjected to a 12% oxygen atmosphere for 35 minutes. Fifteen minutes after insult, rats of one group received an initial dose of OTC (12 mmoles/kg body weight) and rats of the other group receive the phosphate-buffered saline vehicle ("saline"). Rats received subsequent doses of OTC (4 mmoles/kg body weight) or saline, as appropriate, every 12 hours for 3 days.

Rats were sacrificed 1 week following insult and brain damage was assessed.

EXAMPLE 2

Oxidative Stress And Inflammation

A total of 54 animals were used to determine the onset of oxidative stress following insult. GSH level, protein carbonyl content and glutathione reductase activity were used as markers of oxidative stress with spinal cord tissue isolated at 1 hour, 3 hours, 6 hours, 24 hours and 48 hours following injury. Rats were transcardially perfused with cold saline, vertebral columns cooled with liquid nitrogen and the following spinal cord segments were isolated: C3, T3, T5, T6, T7, T9 and L4. Spinal cord segments were frozen in liquid nitrogen and stored at −80° C. until analyzed.

GSH was measured using 5,5'-dithio-bis(2-nitrobenzoic) acid-derivatization ("DTNB") followed by HPLC and UV detection. Briefly, tissues were homogenized in 5% sulfosalicylic acid containing 0.2 mM EDTA and additionally sonicated (3×5 sec, with intermittent cooling). The homogenates were centrifuged at 10,000 g for 15 min and supernatants collected, derivatized and analyzed using the Shimadzu reversed-phase HPLC with ultraviolet detection. A final concentration of 3500 nmoles DTNB was used per reaction for a total volume of 1 ml. Data were collected digitally with Shimadzu Ezchrom Version 3.2 chromatography software. GSH content in rat spinal segments was expressed in micromoles/g wet weight.

Protein carbonyl content was determined spectrophotometrically using 2,4-dinitrophenylhydrazine (DNPH) to trap carbonyls with the adduct formed measured at 360 nm. Results are expressed as pmoles of DNPH incorporated per mg of protein calculated using a molar absorption coefficient of 22,000 $M^{-1}$ $cm^{-1}$ for aliphatic hydrazones.

Glutathione reductase was calculated by measuring the disappearance of NADPH (SIGMA (trade-mark)) in the presence of oxidized-glutathione based upon the procedure described by Eklow et al. (*Eur. J. Biochem.* 138, 459–463 (1984)), as applied in Juurlink et al (*Glia* 22, 371–378, 1998)).

Insult resulted in a rapid and extensive onset of oxidative stress as determined by GSH measurements. The results are depicted in FIG. 1 showing spinal cord GSH levels in control non-traumatized animals and in traumatized animals at different times post-trauma. Data are means±SEM. Within 1 hour GSH has dropped significantly at T5 (P<0.001), T6 (P<0.001), T7 (P<0.001) and T9 (P<0.05). By 48 hours GSH had significantly dropped at C3 (P<0.01), T3 (P<0.05), T9 (P<0.001) and L4 (P<0.001). (One-factor ANOVA with post-hoc Bonferroni test, with time as the dependent variable).

Figure 2:
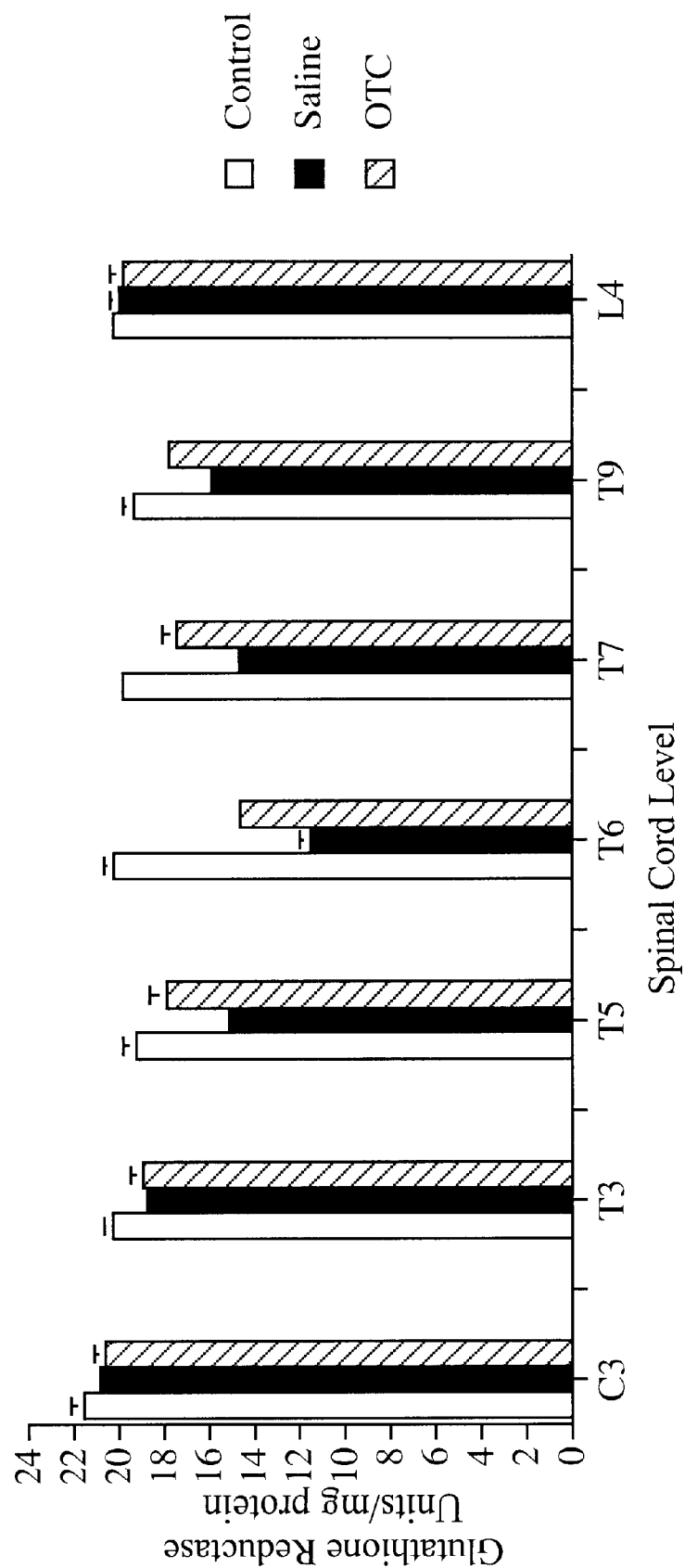
FIG. 2 is a graphical representation of the results of Example 2.

In saline treated animals GSH content at the site of injury, T6, was reduced to less than half of the normal within 1 hour of neurotrauma, with immediately adjacent segments having almost as large a drop in GSH. Over the next 48 hours there were further decreases in spinal cord GSH with sites as distant as C3 and L4 experiencing significant decreases. Laminectomy without spinal cord crush (control) caused a small (10%) drop in GSH at T6 but had no effect upon other levels of the spinal cord (results not presented). The large decrease in GSH at the site of injury and adjacent segments was correlated with a significant decrease in activity of glutathione reductase 24 hours post-trauma in spinal cord segments T3 to T9. Results are depicted in FIG. 2, showing spinal cord glutathione reductase activity under control conditions and 24 hours following spinal cord injury with either saline vehicle or OTC treatment. Data are means±SEM. Spinal cord injury with saline vehicle treatment caused a significant decrease in glutathione reductase activity at T3 (P<0.05), T5 (P<0.01), T6 (P<0.001), T7 (P<0.001) and T9 (P<0.001). Treatment with OTC significantly inhibited the decrease in glutathione reductase activity at T5 (P<0.05), T6 (P<0.01), T7 (P<0.01), and T9 (P<0.01). (One-tailed Student's t test.)

Figure 3:
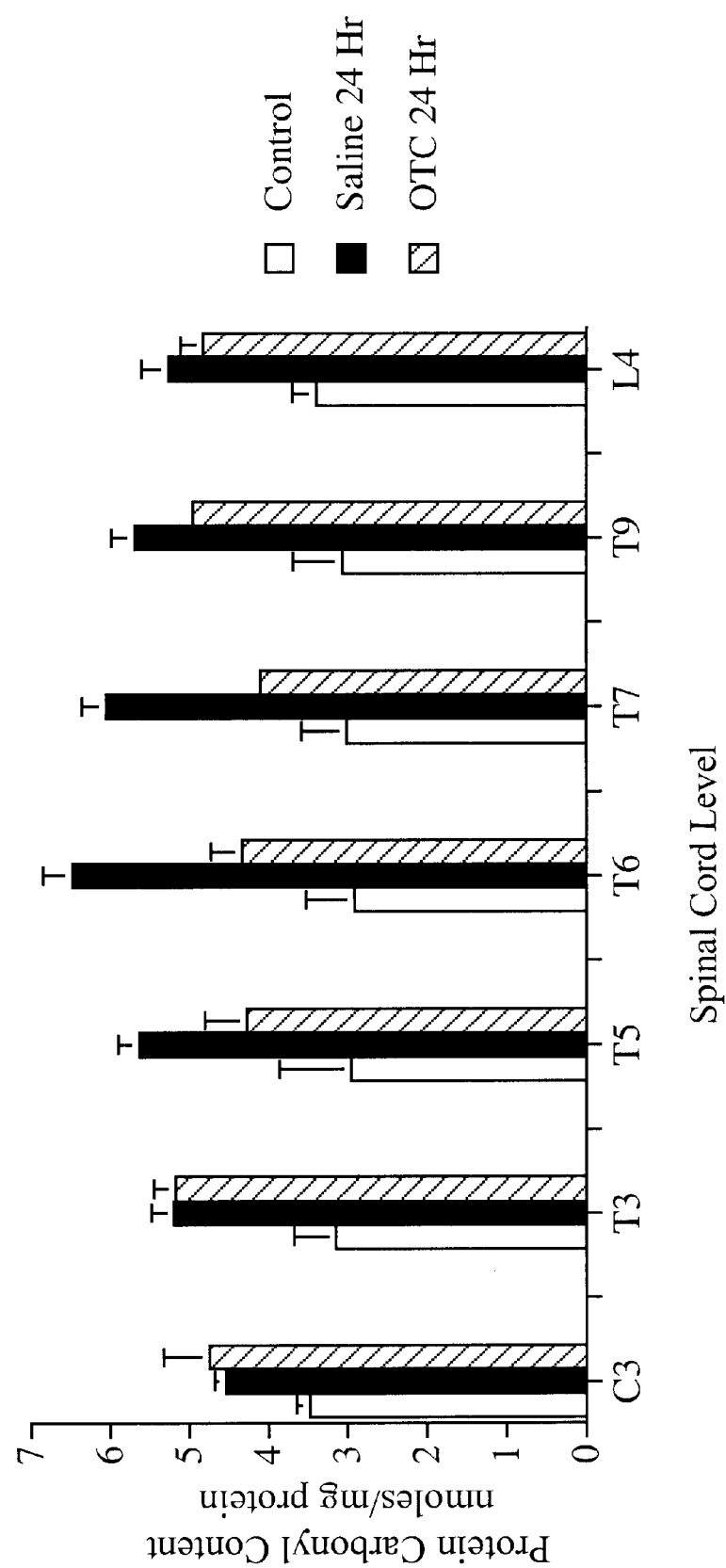
FIG. 3 is a graphical representation of the results of Example 2.

Protein carbonyls were significantly increased in spinal cord levels T3–T9 examined 24 hours following insult with the site of injury and immediately adjacent segments experienced the greatest increase in protein carbonyls. Results are depicted in FIG. 3 showing spinal cord protein carbonyl content under control conditions and 24 hours post-trauma in saline- and OTC-treated animals. Data are means±SEM. Using a one-tailed Student's t test, spinal cord trauma caused a significant increase in protein carbonyl at T3 (P<0.01), T5 (P<0.001), T6 (P<0.001), T7 (P<0.001), T9 (P<0.001) and L4 (P<0.001), while addition of OTC significantly decreased protein carbonyl formation at T5 (P<0.05), T6 (P<0.01), T7 (P<0.01), and T9 (P<0.05).

Figure 4:
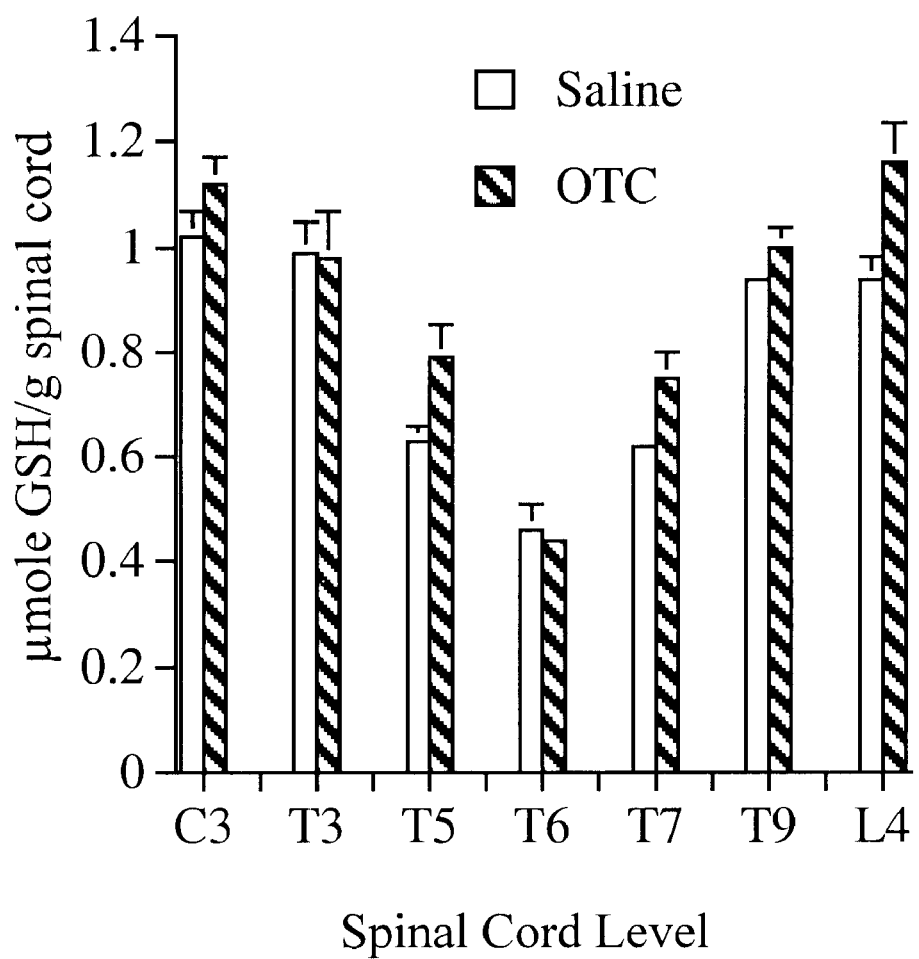
FIG. 4 is a graphical representation of the results of Example 2.

Administration of OTC following insult increased GSH levels in the affected CNS region. These results are depicted in FIG. 4 showing GSH content 26 hours following injury and 2 hours following OTC administration, comparing saline vehicle treatment with OTC treatment. Data are means±SEM. A Wilcoxon spinal cord segment paired non-parametric two-tailed test indicated that GSH levels were significantly different (P=0.0033) in the OTC-treated compared to the saline-treated group of rats.

Administration of OTC following insult also resulted in higher glutathione reductase activity (FIG. 2) and decreased protein carbonyl content (FIG. 3) in comparison to animals given the saline vehicle.

Oxidative stress is also observed following insult by a vascular event. The administration of OTC following insult results in higher concentrations of GSH in the affected CNS regions of OTC-treated animals compared to saline-treated animals. Thus, the administration of OTC reduces oxidative stress following acute physical insult to the CNS, by both neurotrauma and by a vascular event.

Inflammation was assessed by observation and by measurement of ICAM-1 and iNOS levels. A significant increase in inflammation was observed following insult. The administration of OTC following insult results in lower levels of inflammation, compared to saline-treated controls.

EXAMPLE 3

Measurement of Functional Recovery

For behavioral studies animals were randomly assigned to one of three groups: 1) animals that had no surgery; 2) animals with surgery and spinal cord compression that received OTC and 3) animals that received surgery and spinal cord compression that received the saline vehicle only.

Three behavioral tests were used: the angleboard method (Rivin et al., *J. Neurosurg.* 47, 577–581, 1977), a modified Tarlov score (Tariq et al., *J. Neurotrauma*, 15, 239–251, (1998)) and the Basso-Beattie-Bresnahan (BBB) open field locomoter rating scale (Basso, et al., *J. Neurotrauma*, 12, 1–21, 1995)).

The inclined plane is a behavioral task that accesses the animal's ability to maintain its position on a rubber corrugated board; this board was raised at 5° increments. The maximum angle at which an animal can support its weight for 5 sec is the capacity angle.

A semiquantitative assessment of hindlimb function during open field walking gas performed using the modified Tarlov score (Tariq et al.). Spontaneous activity of hind limb was scored as follows: 0=total paraplegia of hindlimbs; 1=no spontaneous movements but responds to hindlimb pinch; 2=spontaneous movement; 3=able to support weight but unable to walk; 4=walks with gross deficit; 5=walks with mild deficit on broad flat surface, 6=able to walk on broad flat surface and support weight on a 1.8 cm wide ledge; 7=walks on ledge.

The procedures for the open field training and testing of the BBB score as described in Basso et al. were acquired only part way through the study; hence, BBB testing was done on only 11 saline-treated and 7 OTC-treated animals. The scale has 22 levels that range from 0 (=total paralysis) to 21 (=normal locomotion). Briefly, rats were gentled and adapted to the open field during the fifth week post-surgery and animals tested at 6 weeks.

Figure 7:
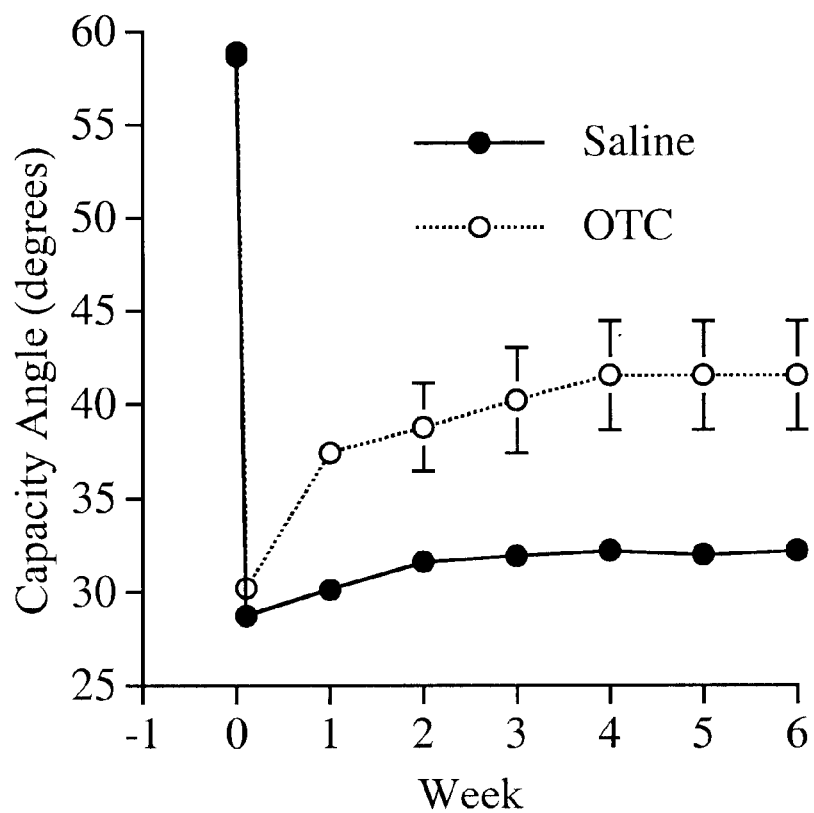
FIG. 7 is a graphical representation of the results of Example 3.
Figure 8A:
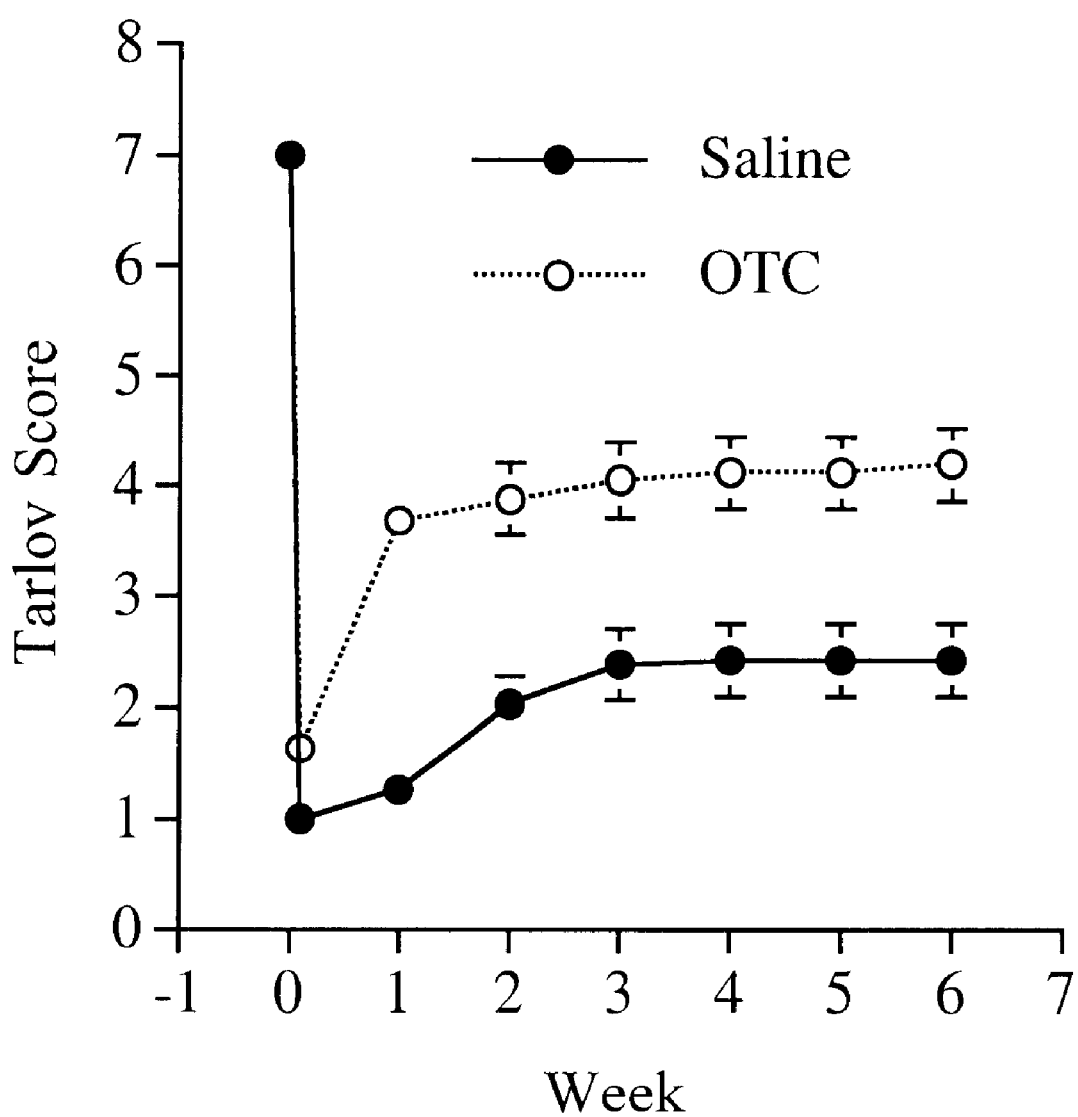
FIGS. 8A and B are graphical representations of the results of Example 3.
Figure 8B:
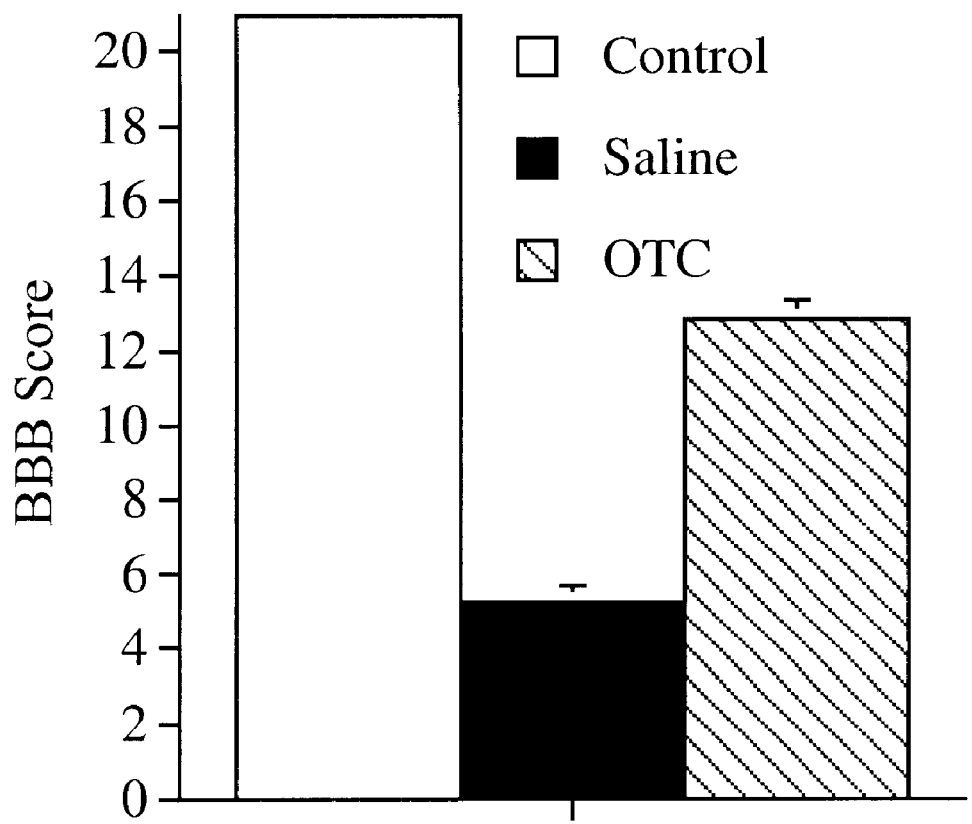

Insult caused a decrease in angleboard capacity angle from 59° to 28° (FIG. 7); during the 6 weeks recovery in saline-treated animals this increased to 32° while in OTC-treated animals this increased to 42° (FIG. 7). Trauma decreased the Tarlov score from 7 to 1 (FIG. 8*a*). Over the next 6 weeks, saline-treated animals increased their Tarlov score to 2.4 whereas OTC-treated animals increased to 4.1. BBB scores for 6 weeks recovery are given in FIG. 8*b*. The behaviour of animals that underwent laminectomy without spinal cord crush was examined after 1 week. In these animals Tarlov score was 6.93±0.06, which was not significantly different from the 7.0 before the laminectomy and capacity angle was 57.2±1.0 which was not significantly different from the 58.2±0.3 prior to the laminectomy.

Dealing specifically with each of the time points mentioned above, FIG. 7 depicts angleboard scores (means±SEM) of animals prior to and following spinal cord crush in animals treated with saline vehicle and OTC. Using ANOVA and post hoc Bonferroni test, the capacity angles between saline treated and OTC treated are significantly different from 1 week onwards (P<0.01). FIG. 8 depicts behavioural scores of animals prior to and following spinal cord injury. A: Tarlov scores between saline (n=15) and OTC-treated (n=12) animals are significantly different from 1 week onwards (P<0.001: One way ANOVA with a post hoc Bonferroni test). B: BBB scores of the same animals at 6 weeks following injury. OTC-treated animals (n=7) have a significantly better BBB Score than saline-treated animals (n=11) (P<0.0001, two-tailed Student's t-test).

Beneficial therapeutic effects of OTC administration are seen with initial doses as low as 0.5 mmole/kg body weight and as high as 20 mmole/kg body weight.

Good therapeutic effects of OTC administration are seen with initial doses as low as 1 mmole/kg body weight and as high as 12 mmoles/kg body weight.

EXAMPLE 4

Spinal Cord Histomorphometry

Following 6 weeks of behavioral evaluation, the spinal cords were fixed by transcardial perfusion with 0.03M phosphate-buffered saline (pH 7.4) containing 1% sodium nitrite in rats anesthetized with Halothane, followed by perfusion (100 ml/100 g) with either 4% formaldehyde (freshly prepared from paraformaldehyde) or FAM solution (formaldehyde, acetic acid and methanol in 1:1:8 ratio) and left in the same fixative for 5 days. Spinal cord segments were isolated from each animal, embedded in paraffin, cut into 15 μm thick sections, stained for myelin with luxol fast blue and counterstained with cresyl violet. Spinal cord tissue staining deep blue was interpreted as being intact while matter. Area of white matter was quantified using Northern Eclipse™ software and expressed in pixels.

The decrease in oxidative stress following OTC administration was associated with sparing of white matter at T6 as indicated by luxol fast blue staining. Luxol fast blue is a classical myelin stain. Six weeks after injury the stained myelin will be associated with intact axons. Hence, luxol fast blue staining is an incident measure of intact axons with cross-sectional area of staining being correlated with total number of intact axons. In the OTC treated animals measured, the average amount of white matter spared ranged from between 10.5 and 26% in comparison to less than 1% in the saline-treated animals. The level of sparing observed in the OTC treated animals is surprising as the crush insult was severe. No grey matter was retained at T6. Sparing of white matter in OTC-treated animals allowed significant functional recovery with animals attaining BBB scores ranging from 11 to 14 in comparison to an average score of 5.3 with saline-treated animals.

Figure 5:
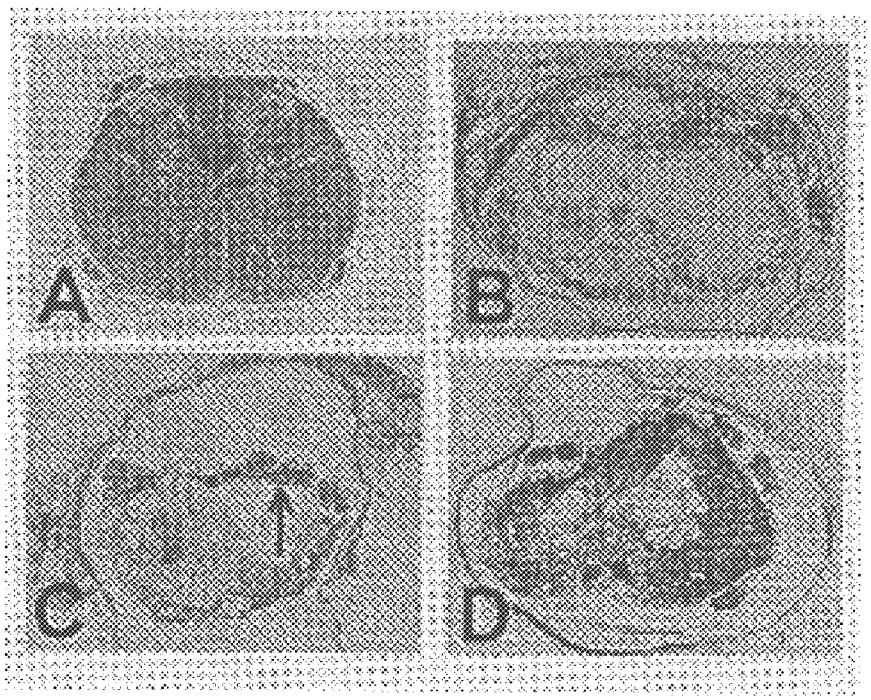
FIG. 5 is a pictorial depiction of the results of Example 4.

Six weeks following spinal cord crush in saline-treated animals much of the T6 spinal cord was occupied by a large cystic cavity with no grey matter evident and less than 1% of white matter remaining. Results are depicted in FIG. 5 showing photomicrographs of T6 spinal cords stained with cresyl violet and luxol fast blue. Dorsal is at the top. A: Control spinal cord with dorsal and ventral roots evident below dura mater. The remaining spinal cords were fixed 6 weeks following spinal cord trauma. B: Typical example of a spinal cord from a saline-treated animal with a BBB score of 4. Much of T6 spinal cord is cystic. Although myelinated dorsal and ventral roots are evident, there is little spinal cord luxol fast blue positive central myelin. C: Spinal cord from an OTC-treated animal with a BBB score of 11. Although cystic, a thin rim of myelinated axons is evident in the spinal cord. Arrow indicates a region with substantial amount of white matter retained. D: Spinal cord from an OTC-treated animal with a BBB score of 14. A larger production of myelinated axons is retained in this spinal cord.

Administration of OTC did not result in grey matter sparing at T6, but a peripheral rim of white matter was observed at T6 in all spinal cords examined from animals that were administered OTC (FIG. 5).

Figure 6:
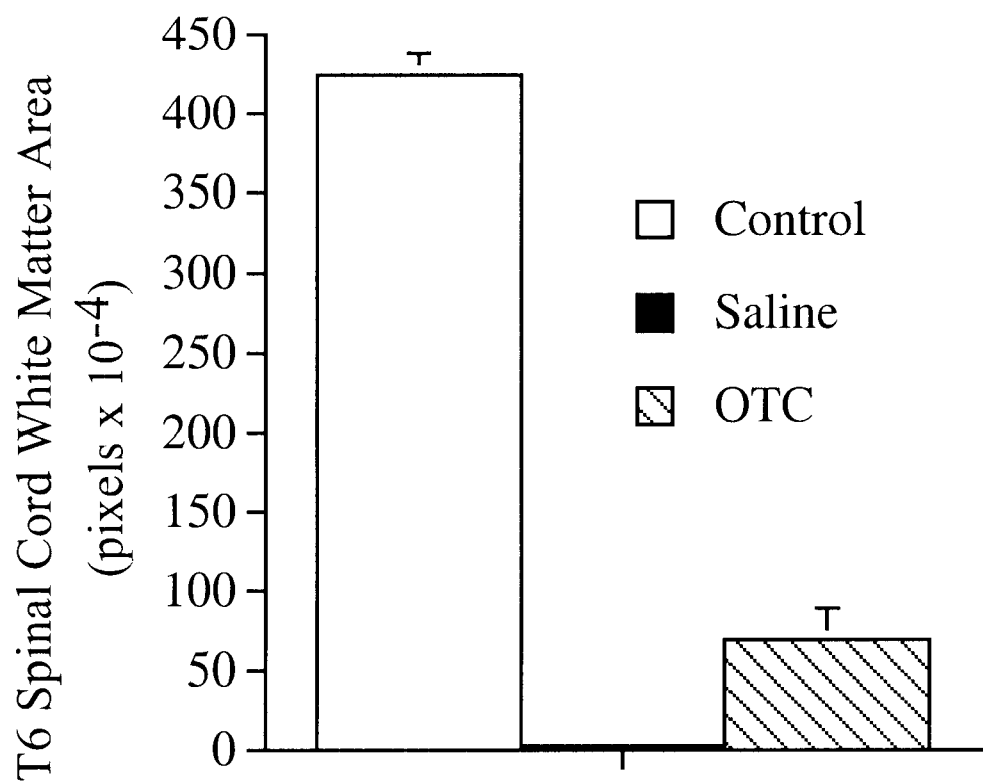
FIG. 6 is a graphical representation of the results of Example 4.

The amount of white matter retained varied from 10.5 to 26% of the control value. These results are depicted in FIG. 6 showing a graph depicting area of white matter in pixels at mid T6 spinal cord segment in control as well as saline-treated and OTC-treated animals that underwent spinal cord crush at T6. Data represent means±SEM. OTC-treated animals have significantly more luxol fast blue stained material than saline-treated animals ($P<0.05$, two-tailed Welch's t-test).

EXAMPLE 5

Brain Damage Assessment Following a Vascular Event

Brain damage following a vascular event was assessed using the method of Thornhill, et al. (*Brain Res.* 825(1–2):36–45 (1999)).

Figure 9:
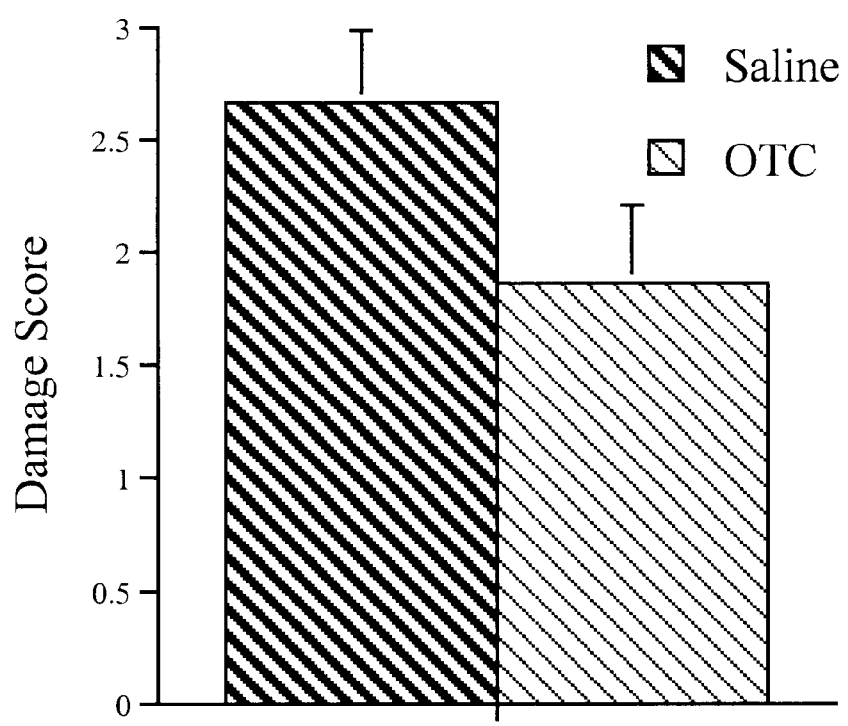
FIG. 9 is a graphical representation of the results of Example 5.

The OTC-treated animals (score 1.86) had less brain damage than the saline-treated animals (score 2.67). Functional recovery is better in OTC-treated animals. Thus, the administration of OTC enhances functional recovery from acute physical insult to the CNS by way of a vascular event. The results of this experiment are depicted in FIG. 9.

Thus, it will be apparent that there has been provided a method of improving functional recovery from insult.

We claim:

1. A method of promoting functional recovery from damage caused by disruption of normal blood flow arising from an acute physical insult to the central nervous system, comprising administering to a mammalian patient which has suffered the acute physical insult to the central nervous system, after the physical insult, an initial dose of L-2-oxothiazolidine-4-carboxylate (OTC), or an ester or pharmaceutically acceptable salt of OTC having the biological activity of OTC.

2. The method of claim 1 further including the step of administering a number of subsequent doses of OTC, or an ester or a pharmaceutically acceptable salt of OTC having the biological activity of OTC, at subsequent time periods.

3. The method of claim 2 wherein the initial dose is administered within a first time period of up to 24 hours following the insult.

4. The method of claim 3 wherein the first time period is up to 12 hours following the insult.

5. The method of claim 4 wherein the first time period is up to 6 hours following the insult.

6. The method of claim 5 wherein the first time period is up to 2 hours following the insult.

7. The method of claim 1 wherein the initial dose is between about 0.5 and 20 mmoles/kg body weight.

8. The method of claim 2 wherein the initial dose is between about 0.5 and 20 mmoles/kg body weight.

9. The method of claim 1 wherein the initial dose is between about 1 and 12 mmoles/kg body weight.

10. The method of claim 2 wherein each subsequent dose is independently selected to be between about 0.5 and 5 mmoles/kg body weight.

11. The method of claim 2 wherein the number of subsequent doses is between about 3 and 15.

12. The method of claim 2 wherein each subsequent time period is independently selected to be between about 4 and 16 hours.

13. The method of claim 1 wherein the initial dose comprises OTC.

14. The method of claim 2 wherein the initial dose comprises OTC.

15. The method of claim 1 wherein the initial dose comprises an ester or pharmaceutically acceptable salt of OTC having the biological activity of OTC.

16. The method of claim 2 wherein the initial dose comprises an ester or pharmaceutically acceptable salt of OTC having the biological activity of OTC.

17. The method of claim 2 wherein the subsequent dose comprises OTC.

18. The method of claim 2 wherein the subsequent dose comprises an ester or pharmaceutically acceptable salt of OTC having the biological activity of OTC.

19. The method of claim 1 wherein the insult is neurotrauma.

20. The method of claim 2 wherein the insult is neurotrauma.

21. The method of claim 1 wherein the insult is a vascular event.

22. The method of claim 2 wherein the insult is a vascular event.

23. A method of reducing oxidative stress in the central nervous system of a mammalian patient caused by disruption of normal blood flow arising from an acute physical insult to the central nervous system of the patient, comprising administering to the patient following the insult an initial dose of L-2-oxothiazolidine-4-carboxylate (OTC), or an ester or pharmaceutically acceptable salt of OTC having the biological activity of OTC.

24. The method of claim 23 further including the step of administering a number of subsequent doses of OTC, or an ester of pharmaceutically acceptable salt of OTC having the biological activity of OTC at subsequent time periods.

25. A method of reducing inflammation in the central nervous system of a mammalian patient caused by disruption of normal blood flow arising from an acute physical insult to the central nervous system of the patient, comprising administering to the patient following the insult an initial dose of L-2-oxothiazolidine-4-carboxylate (OTC), or an ester or pharmaceutically acceptable salt of OTC having the biological activity of OTC.

26. The method of claim 25 further including the step of administering a number of subsequent doses of OTC or an ester or pharmaceutically acceptable salt of OTC having the biological activity of OTC at subsequent time periods.

27. The method of claim 25 wherein the initial dose is a dose of OTC.

28. The method of claim 25 further including a step of administering methylprednisolone.

29. The method of claim 26 wherein the subsequent doses are subsequent doses of OTC.

* * * * *